United States Patent [19]

Lang et al.

[11] Patent Number: 5,190,564
[45] Date of Patent: Mar. 2, 1993

[54] PROCESS FOR DYEING KERATINOUS FIBRES COMBINING ISATIN OR ITS DERIVATIVES WITH AN AMINOINDOLE OR AN AMINOINDOLINE, AND COMPOSITIONS USED

[75] Inventors: Gérard Lang, Saint-Gratien; Jean Cotteret, Verneuil-sur-Seine, both of France

[73] Assignee: L'Oreal, Paris, France

[21] Appl. No.: 828,299

[22] Filed: Jan. 30, 1992

[30] Foreign Application Priority Data

Feb. 1, 1991 [FR] France ............................ 91 01186

[51] Int. Cl.$^5$ ............................................. A61K 7/13
[52] U.S. Cl. ......................................... 8/423; 8/405; 8/406; 8/408; 8/409; 8/429; 424/70; 548/485
[58] Field of Search .................. 8/405, 406, 408, 409, 8/423, 429; 548/485; 424/70

[56] References Cited

U.S. PATENT DOCUMENTS

| | | | |
|---|---|---|---|
| 3,630,655 | 12/1971 | Berth et al. | 8/423 |
| 4,013,404 | 3/1977 | Parent et al. | 8/423 |
| 4,289,495 | 9/1981 | Bugaut et al. | 8/408 |
| 4,330,292 | 5/1982 | Bugaut et al. | 8/409 |
| 4,333,730 | 6/1982 | Bugaut et al. | 8/408 |
| 4,566,875 | 1/1986 | Grollier et al. | 8/408 |
| 4,750,908 | 6/1988 | Rosenbaum et al. | 8/435 |
| 4,888,025 | 12/1989 | Bugaut et al. | 8/408 |
| 4,921,503 | 5/1990 | Anderson et al. | 8/405 |
| 4,932,977 | 6/1990 | Schultz | 8/408 |
| 5,053,053 | 10/1991 | De Labbey et al. | 8/405 |

FOREIGN PATENT DOCUMENTS 0359465 3/1990 European Pat. Off. .
2716671 10/1978 Fed. Rep. of Germany .

OTHER PUBLICATIONS

French Search Report of FR 91 01186.

*Primary Examiner*—A. Lionel Clingman
*Assistant Examiner*—William S. Parks
*Attorney, Agent, or Firm*—Cushman, Darby & Cushman

[57] ABSTRACT

The invention relates to a process for dyeing keratinous fibres, comprising the simultaneous or sequential application of a composition (A) containing a compound of formula (I):

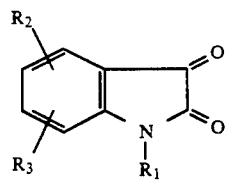

in which:

$R_1$ denotes hydrogen, alkyl, acetyl, benzoyl, phenyl or $C_1$–$C_4$ carboxyalyl (sic);
$R_2$ and $R_3$ denote hydrogen, alkyl, alkoxy, hydroxyalkyl, amino, halogen, nitro, alkylphenyl, phenyl, alkylamino, hydroxyalkylamino;

and a composition (B) containing at least one compound of formula (II):

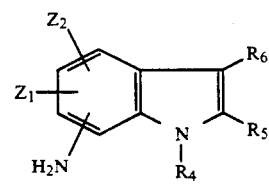

in which:

$R_4$ and $R_6$ denote hydrogen, alkyl;
$R_5$ denotes hydrogen, alkyl, COOR' where R' is hydrogen or alkyl;
$Z_1$ represents hydrogen, halogen, alkyl, alkoxy or hydroxyl;
$Z_2$ represents hydrogen or alkyl or a compound of formula (III):

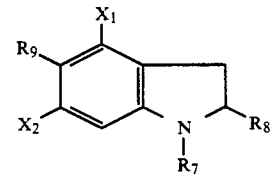

in which:

$R_7$ and $R_8$ denote hydrogen or alkyl;
$X_1$ and $X_2$ represent hydrogen or an $NH_2$ radical;
$R_9$ denotes hydrogen, alkyl, alkoxy;
as well as the compositions used.

17 Claims, No Drawings

PROCESS FOR DYEING KERATINOUS FIBRES COMBINING ISATIN OR ITS DERIVATIVES WITH AN AMINOINDOLE OR AN AMINOINDOLINE, AND COMPOSITIONS USED

The present relates to a process for dyeing keratinous fibers, in particular human hair, combining isatin or one of its derivatives with an aminoindole or an aminoindoline, as well as the compositions used.

The use of isatin as a yellow dye base has already been proposed in French Patent No. 2,588,473 for direct hair dyeing, that is to say in a dyeing process not using an oxidative dye developing process.

European Application No. 0,359,465 subsequently proposed a direct dyeing process using isatin or one of its derivatives in combination with disubstituted aminobenzene derivatives.

Surprisingly, the Applicant has just discovered a novel dyeing process combining isatin or its derivatives with aminoindole or aminoindoline type dyes which make it possible to obtain a wide range of shades which are more resistant to shampooing and to transpiration than those obtained by direct dyeing processes using amino derivatives known from the prior art. The colourings obtained are further more stable to light, to adverse weather conditions and to chemical agents.

The subject of the present invention is therefore a process for dyeing keratinous fibers which consists in applying isatin or one of its derivatives and an aminoindole or an aminoindoline to the fibers, either simultaneously in the form of a freshly prepared mixture, or successively.

A subject of the invention also consists of a two-component dyeing agent.

Other subjects will emerge from the description.

The process for dyeing keratinous fibers, in particular human hair, in accordance with the present invention, is essentially characterised in that it comprises applying to the said fibers a component (A) consisting of a composition containing, in a medium suitable for dyeing, at least one compound of the following formula (I):

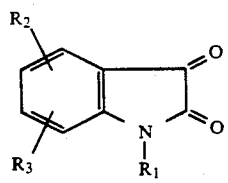

(I)

in which:
$R_1$ denotes a hydrogen atom, a $C_1$-$C_6$ alkyl radical, acetyl, benzoyl, phenyl or $C_1$-$C_4$ carboxyalkyl;
$R_2$ and $R_3$, independently of each other, denote a hydrogen atom, a $C_1$-$C_6$ alkyl, $C_1$-$C_4$ alkoxy, a hydroxyl, an amino, a halogen atom, a nitro, an alkyl($C_1$-$C_6$)phenyl, phenyl, alkyl($C_1$-$C_6$)amino, hydroxyalkyl($C_1$-$C_6$)amino, polyhydroxyalkyl($C_2$-$C_6$)amino group;
and a component (B) consisting of a composition containing, in a medium suitable for dyeing, at least one aminoindole of the following formula (II):

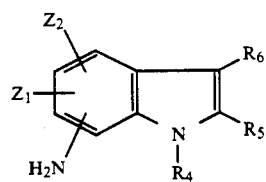

(II)

in which:
$R_4$ and $R_6$, independently of each other, represent a hydrogen atom or a $C_1$-$C_4$ alkyl group;
$R_5$ denotes a hydrogen atom or a $C_1$-$C_4$ alkyl group or a COOR' group, R' being a hydrogen atom or a $C_1$-$C_4$-alkyl group;
$Z_1$ represents a hydrogen or a halogen atom, a $C_1$-$C_4$-alkyl, $C_1$-$C_4$ alkoxy or hydroxyl radical;
$Z_2$ represents a hydrogen atom or a $C_1$-$C_4$ alkyl radical;
as well as its cosmetically acceptable salts, or alternatively an aminoindoline of formula (III):

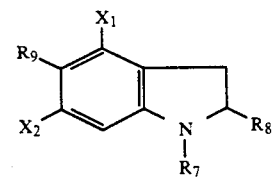

(III)

in which:
$R_7$ and $R_8$, independently of each other, represent a hydrogen atom or a $C_1$-$C_4$ alkyl radical;
$X_1$ and $X_2$ represent a hydrogen atom or an $NH_2$ radical, at least one, and only one, representing $NH_2$;
$R_9$ denotes a hydrogen atom, a $C_1$-$C_4$ alkyl or $C_1$-$C_4$-alkoxy radical; $R_9$ denoting hydrogen when $X_2$ denotes $NH_2$;
as well as its cosmetically acceptable salts.

The process according to the invention may be implemented without using an oxidising agent other than air.

The dyeing process described above results in the formation of a Schiff base, either during the mixing of the composition (A) with the composition (B), or in situ in the keratinous fiber during a sequential application of the compositions (A) and (B). This Schiff base is of the formula:

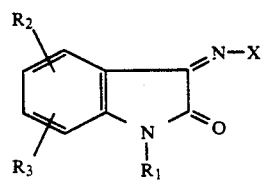

(IV)

in which X denotes:

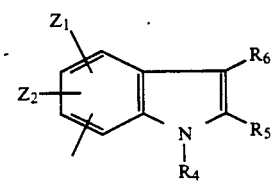

a)

or

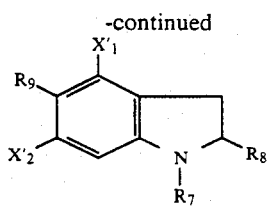

b)

$R_1$ to $R_9$, $Z_1$ and $Z_2$ have the meanings given above for the formulae (I), (II) and (III);

$X'_1$ and $X'_2$ denote a hydrogen atom or a covalent bond, at least one, and only one, denoting a hydrogen atom; $R_9$ denoting hydrogen when $X'_2$ represents a covalent bond.

Among the compounds of formula (I), isatin may be more particularly mentioned.

The preferred compounds of formula (II) are chosen from:
4-aminoindole
5-aminoindole
7-aminoindole
2,3-dimethyl-5-amino-6-hydroxyindole
2,3-dimethyl-5-amino-6-methoxyindole
2,3-dimethyl-5-chloro-6-aminoindole
2,3,4,5-tetramethyl-6-aminoindole
2,3-dimethyl-5-methoxy-6-aminoindole
2,3-dimethyl-5-ethyl-6-aminoindole
2-methyl-6-aminoindole The compounds of formula (II) which are more particularly preferred are chosen from:
6-aminoindole
2,3-dimethyl-5-hydroxy-6-aminoindole
2,3,5-trimethyl-6-aminoindole
2-methyl-5-hydroxy-6-aminoindole
2,3-dimethyl-6-aminoindole
2,3,7-trimethyl-6-aminoindole
2,3,4-trimethyl-6-aminoindole The preferred compounds of formula (III) are chosen from 6-aminoindoline and N-ethyl-6-aminoindoline.

According to the process of the present invention, the compound of formula (I) is preferably present in the component (A) in proportions of between 0.01 and 5% by weight and more particularly between 0.25 and 2% by weight relative to the total weight of the component (A) or the components (A)+(B), and the compound of formula (II) or (III) is present in the component (B) in proportions preferably of between 0.01 and 5% by weight and in particular between 0.25 and 2% by weight relative to the total weight of the component (B) or the components (A)+(B).

The compositions (A) and (B) which may be used in accordance with the invention are more or less thickened, aqueous or anhydrous liquid compositions, creams, aqueous or anhydrous gels, oils or powders to be diluted with a liquid at the time of use, alternatively called "cataplasms".

In a first embodiment of the invention, the cosmetic medium suitable for dyeing is aqueous and has a pH which may vary between 2 and 10, and preferably between 3 and 9.5, it is adjusted to the desired value using alkalinising agents or acidifying agents which are known per se.

These compositions may contain anionic, cationic, nonionic or amphoteric surface-active agents or their mixtures. These surface-active agents are present in the compositions conforming to the invention in proportions of between 0.1 and 55% by weight, preferably between 1 and 40% by weight relative to the total weight of each composition.

These aqueous compositions may contain organic solvents among which there may be mentioned by way of example, lower alkanols such as ethanol or isopropanol, polyols such as glycerol, glycols or glycol ethers such as ethylene glycol, propylene glycol, ethylene glycol monobutyl ether and diethylene glycol monoethyl ether and monomethyl ether as well as similar products or their mixtures.

These solvents are preferably used in proportions ranging from 1 to 60% by weight, and more particularly from 3 to 30% by weight relative to the total weight of the composition.

These compositions may be thickened using agents chosen from sodium alginate, gum arabic, guar or carob gum, xanthan gum, pectins, cellulose derivatives and various polymers having a thickening role such as acrylic acid derivatives. Inorganic thickening agents such as bentone may also be used.

These thickening agents are preferably present in proportions of between 0.1 and 5% by weight, and in particular between 0.5 and 3% by weight relative to the total weight of the composition.

These compositions may also contain anionic, nonionic, cationic or amphoteric polymers or their mixtures in proportions of 0.1 to 5% by weight relative to the total weight of the composition.

These compositions may of course contain all the other adjuvants normally used in compositions for hair dyeing, such as penetrating agents, sequestering agents, antioxidants, buffers, perfumes, dyes and the like.

A preferred form of the invention consists in using an anhydrous medium such as described in French Patent No. 2,526,031.

Anhydrous medium is understood as meaning a medium containing not more than 1% of water.

In accordance with this variant of the invention, the anhydrous medium consists of a mixture of at least one anhydrous solvent and one or more anhydrous surface-active agents such that these compositions contain at least 15% of solvent and at least 20% of surface-active agent.

The solvents used are cosmetically acceptable solvents chosen from $C_2$–$C_{20}$ saturated monoalcohols such as ethanol, isopropanol, cetyl alcohol or octyldodecanol; polyols such as alkylene glycols such as ethylene glycol, propylene glycol, glycerol, diethylene glycol; glycol ethers such as mono-, di- and triethylene glycol monoalkyl ethers such as for example ethylene glycol monoethyl ether, ethylene glycol monobutyl ether, diethylene glycol monoethyl ether; esters such as for example ethylene glycol monomethyl ether acetate, ethylene glycol monoethyl ether acetate; esters of fatty acids and saturated lower alcohols such as isopropyl myristate or palmitate.

The compositions which are particularly preferred contain a solvent chosen from ethanol, cetyl alcohol, propylene glycol, ethylene glycol monoethyl ether or ethylene glycol monobutyl ether.

The surface-active agents used in this embodiment are chosen from anhydrous surface-active agents of the anionic, nonionic, cationic or amphoteric type or their mixtures. There may be mentioned more particularly polyoxyethylenated fatty alcohols, polyoxyethylenated alkylphenols or naphthols, monoalkyltrimethylammonium halides, dialkyldimethylammonium halides, soaps, polyglycerolated fatty alcohols. The preferred surface-active agents are nonionic surface-active agents.

These compositions may contain an anhydrous alkaline or acidifying agent such as for example citric acid, ascorbic acid, acetic acid, lactic acid and alkanolamines such as, preferably, those which are completely substituted on the amine group, such as dimethylaminoethanol.

In addition to the compounds described above, the anhydrous compositions conforming to the invention may contain numerous additives usable in cosmetics on the one condition that they contain less than 1% of water. Among these additives, there may be mentioned perfumes, thickening agents, processing agents, antioxidants, vegetable or mineral oils, preserving agents and organic salts.

These compositions may be applied to wet hair as they are or they may be diluted immediately before use. In the latter case, the compositions according to the invention are diluted, at the time of dyeing, with an aqueous solution such that the ratio between the composition conforming to the invention and the aqueous solution is between 0.25 and 2. The aqueous solution may be prepared using pure water, but also using any other more or less thickened, complex aqueous liquid such as for example a carrier normally used in hair dyeing compositions.

In this case, the components of the cosmetic medium may be all types of cosmetically acceptable ingredients, anhydrous or not, normally used in this type of composition and described above in a general manner.

Another method of use of the compositions (A) and/or (B) conforming to the invention consists in their use in the form of cataplasmas, that is to say in the form of a powder to be diluted with a liquid at the time of use.

In this embodiment, the dyes are prepared in the form of a powder which is stable during storage, and are introduced into a solid medium which may consist of powders, flours, starchy or mucilaginous substances which are diluted at the time of use with a suitable liquid in order to form a mixture with an appropriate consistency for applying to the head.

The powders or flours used in this type of composition generally consist of insoluble substances such as silicas, clays, plants pulverised after extracting their active ingredients with a solvent.

The liquid may consist of water or mixtures of water and cosmetically acceptable solvents such as alcohols or glycols or alternatively oils.

The liquid medium is added to the powder in proportions such that a paste with a viscosity of between 0.3 and 5 Pa.s is obtained after mixing.

A subject of the invention consists of a dyeing agent for keratinous fibers, in particular human hair, characterised in that it consists of the components (A) and (B) stored in separate forms such as defined above.

The components (A) and (B) are intended either to be mixed immediately before use, or to be successively applied to the fibers to be treated.

According to one embodiment, the different components (A) and (B) are packaged in a multi-compartment device also called "dyeing kit" containing all the components intend to be applied, for the same dye, to the keratinous fibers, in particular hair, in successive applications with or without premixing.

Such devices may comprise a first compartment containing the composition (A) which contains isatin or its derivatives of formula (I) and a second compartment comprising the composition (B) which contains the aminoindole of formula (II) or the aminoindoline of formula (III).

Another variant may also consist in storing the composition (A) or the composition (B) in an anhydrous solvent medium, and in providing a third compartment containing an aqueous medium which is suitable for dyeing and is cosmetically acceptable. In this case, the content of the third compartment is mixed immediately before use in one or the other, or both compartments containing the anhydrous compositions (A) and (B) or, alternatively, the three compartments are mixed before use.

According to a variant, the process of the invention consists in mixing immediately before use the composition (A) with the composition (B), the resulting composition being applied to the hair for 5 to 40 minutes and, preferably, 20 to 30 minutes. The hair is then rinsed, washed with shampoo, rinsed again and then dried.

According to another variant, the process of the invention consists in applying to the hair at least one composition (A) and one composition (B) such as defined above; in leaving each of them in contact for 5 to 40 minutes, preferably 20 to 30 minutes and in optionally rinsing with water between the two stages. The hair is then rinsed, washed with shampoo, rinsed again and then dried.

The following examples are intended to illustrate the invention with no limitation being implied.

EXAMPLES 1 to 9

The hair is dyed by applying 20 g of the compositions to natural grey hair which is 90% white.

The compositions are prepared immediately before use. The composition in Example 9 is mixed with 1.5 times its weight of water at the time of use (pH 9).

The composition is allowed to act for 20 minutes and the hair is then rinsed, shampooed and rinsed again. After drying, the hair is dyed to the shade specified at the bottom of the table below.

TABLE I

| in g AS | 1 | 2 | 3 | 4 | 5 |
|---|---|---|---|---|---|
| Isatin | 1 | 1 | 1 | 1 | 1 |
| 6-Aminoindole | 1 | | | | |
| 2,3-Dimethyl-5-hydroxy-6-aminoindole, 2 HBr | | 1 | | | |
| 2,3,5-Trimethyl-6-aminoindole | | | 1 | | |
| 2,3,7-Trimethyl-6-aminoindole | | | | 1 | |
| 2,3,4-Trimethyl-6-aminoindole | | | | | 1 |
| Ethyl alcohol | 30 | 30 | 30 | 30 | 30 |
| Triethanolamine qs pH | | 7.5 | 7.5 | | 7.3 |
| Spontaneous pH | 8.1 | | | 7.5 | |
| Water qs | 100 | 100 | 100 | 100 | 100 |
| Shades obtained | intense coppery | dark purple | red coppery | beige iridescent blond | red iridescent |

| in g AS | 6 | 7 | 8 | 9 |
|---|---|---|---|---|
| Isatin | 1 | 1 | | 1 |
| 6-Bromoisatin | | | 1 | |
| 2-Methyl-5-hydroxy-6-aminoindole | | 1 | | |
| 2,3-Dimethyl-6-aminoindole, HCl | 1 | | 1 | 1 |
| Ethyl alcohol | 30 | 30 | 30 | 28.5 |
| Oxyethylenated nonylphenol con- | | | | 100 |

TABLE I-continued

| | | | | |
|---|---|---|---|---|
| taining 9 moles of ethylene oxide qs | | | | |
| N,N-Dimethylamino-2-ethanol | | | 1 | |
| Triethanolamine qs pH | 7.5 | 7.5 | 8 | |
| Water qs | 100 | 100 | 100 | |
| Shades obtained | red mahogany | mahogany | ashen iridescent | golden light blond |

EXAMPLE 10

The composition is mixed with twice its weight of water at the time of use. 20 g of this mixture (pH 9.3) are applied to natural grey hair which is 90% white.

The composition is allowed to act for 20 minutes and the hair is then rinsed, shampooed and rinsed again. After drying, the hair is dyed to the shade specified at the bottom of Table II below.

EXAMPLE 11

The compositions (A) and (B) are mixed with twice their weight of water at the time of use. 20 g of the composition (A) (pH 8.6) are applied to 3 g of natural grey hair which is 90% white.

The composition is allowed to act for 15 minutes, the hair is rinsed, and then 20 g of the composition (B) (pH 9.2) are applied for 15 minutes, the hair is rinsed, shampooed and rinsed again. After drying, the hair is dyed to the shade specified at the bottom of Table II below.

We claim:
1. Process for dyeing keratinous fibers, in particular human hair, characterised in that there is applied to the said fibers a component (A) consisting of a composition containing, in a medium suitable for dyeing, at least one compound of formula (I):

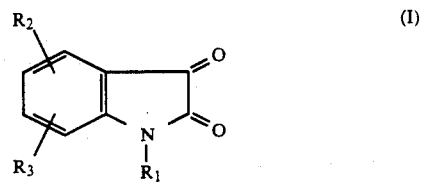

in which:
- $R_1$ denotes a hydrogen atom, a $C_1$-$C_6$ alkyl radical, acetyl, benzoyl, phenyl or $C_1$-$C_4$ carboxyalkyl;
- $R_2$ and $R_3$, independently of each other, denote a hydrogen atom, a $C_1$-$C_5$ alkyl, $C_1$-$C_4$ alkoxy, a hydroxyl, an amino, a halogen atom, a nitro, an alkyl($C_1$-$C_6$)phenyl, phenyl, alkyl($C_1$-$C_6$)amino, hydroxyalkyl($C_1$-$C_6$)amino, polyhydroxyalkyl($C_2$-$C_6$)amino group;

and a component (B) consisting of a composition containing, in a medium suitable for dyeing, at least one aminoindole compound of the following formula (II):

TABLE II

| | | 11 | |
|---|---|---|---|
| in g AS | 10 | Comp. (A) | Comp. (B) |
| Isatin | 4 | 4 | |
| 2,3-Dimethyl-5-hydroxy-6-aminoindole | | | 4 |
| 2,3-Dimethyl-6-aminoindole, HCl | 4 | | |
| Carob gum sold under the name VIDOGUM L 175 by SANOFI BIO INDUSTRIE | 3 | 3 | 3 |
| Calcium carbonate | 8 | 8 | 8 |
| Saponaria extraction residue powder with a particle size of less than 90 microns | 35 | 35 | 35 |
| Skimmed milk powder qs | 100 | 100 | 100 |
| Exposure time (in min) | 15 | 15 | 15 |
| Shades obtained on grey hair which is 90% white | Pink | iridescent blond | |

| in g AS | 12 | 13 | 14 | 15 | 16 | 17 | 18 |
|---|---|---|---|---|---|---|---|
| Isatin | 1 | 1 | 1 | 1 | 1 | 1 | 1 |
| 2,3-Dimethyl-5-ethyl-6-amino-indole, HCl | 1 | | | | | | |
| 2,3,4,5-Tetramethyl-6-amino-indole, HCl | | 1 | | | | | |
| 5-Aminoindole | | | 1 | | | | |
| 7-Aminoindole | | | | 1 | | | |
| 2,3-Dimethyl-6-hydroxy-5-amino-indole | | | | | 1 | | |
| 2,3-Dimethyl-6-methoxy-5-amino-indole, HCl | | | | | | 1 | |
| 6-Aminoindole | | | | | | | 1 |
| Ethyl alcohol | 30 | 30 | 30 | 30 | 30 | 30 | 10 |
| Triethanolamine qs pH | 7.5 | 8.4 | | | | 7.5 | 7.5 |
| Spontaneous pH | | | 8.5 | 7 | 9 | | |
| Water qs | 100 | 100 | 100 | 100 | 100 | 100 | 100 |
| Shades obtained | light coppery red | light iridescent ashen golden blond | golden coppery | golden coppery beige | iridescent coppery | golden coppery | light golden |

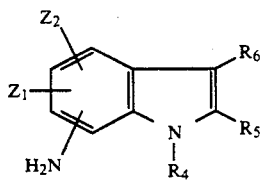

in which:
R$_4$ and R$_6$, independently of each other, represent a hydrogen atom or a C$_1$-C$_4$ alkyl group;
R$_5$ denotes a hydrogen atom or a C$_1$-C$_4$ alkyl group or a COOR' group, R' being a hydrogen atom or a C$_1$-C$_4$ alkyl group;
Z$_1$ represents a hydrogen or a halogen atom, a C$_1$-C$_4$-alkyl, C$_1$-C$_4$ alkoxy or hydroxyl radical;
Z$_2$ represents a hydrogen atom or a C$_1$-C$_4$ alkyl radical;
as well as its cosmetically acceptable salts, or alternatively an aminoindoline of formula (III):

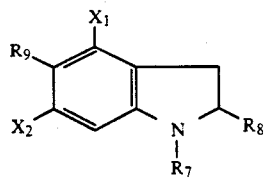

in which:
R$_7$ and R$_8$, independently of each other, represent a hydrogen atom or a C$_1$-C$_4$ alkyl radical;
X$_1$ and X$_2$ represent a hydrogen atom or an NH$_2$ radical, at least one, and only one, representing NH$_2$;
R$_9$ denotes a hydrogen atom, a C$_1$-C$_4$ alkyl or C$_1$-C$_4$-alkoxy radical; R$_9$ denoting hydrogen when X$_2$ denotes NH$_2$;
as well as its cosmetically acceptable salts.

2. Process according to claim 1, characterised in that the compound of formula (I) is isatin.

3. Process according to claim 1, characterised in that the compound of formula (II) is chosen from:
4-aminoindole
5-aminoindole
7-aminoindole
2,3-dimethyl-5-amino-6-hydroxyindole
2,3-dimethyl-5-amino-6-methoxyindole
2,3-dimethyl-5-chloro-6-aminoindole
2,3,4,5-tetramethyl-6-aminoindole
2,3-dimethyl-5-methoxy-6-aminoindole
2,3-dimethyl-5-ethyl-6-aminoindole
2-methyl-6-aminoindole.

4. Process according to claim 1 or 2, characterised in that the compound of formula (II) is chosen from:
6-aminoindole
2,3-dimethyl-5-hydroxy-6-aminoindole
2,3,5-trimethyl-6-aminoindole
2-methyl-5-hydroxy-6-aminoindole
2,3-dimethyl-6-aminoindole
2,3,7-trimethyl-6-aminoindole
2,3,4-trimethyl-6-aminoindole.

5. Process according to claim 1, characterised in that the aminoindoline compound of formula (III) is chosen from 6-aminoindoline or N-ethyl-6-aminoindoline.

6. Process according to claim 1, characterised in that the compound of formula (I) is present in the composition (A) in proportions of between 0.01 and 5% by weight relative to the weight of the composition (A) or to the total weight of (A)+(B) and in that the compound of formula (II) or (III) is present in the composition (B) in proportions of between 0.01 and 5% by weight relative to the weight of the composition (B) or of the total weight of (A)+(B).

7. Process according to claim 1 characterised in that the composition (A) and/or the composition (B) is an aqueous or anhydrous composition in more or less thickened liquid form, a composition in the form of a cream, an aqueous or anhydrous gel, an oil or a powder to be diluted with a liquid at the time of use.

8. Process according to claim 7, characterised in that the composition (A) and/or the composition (B) is present in the form of an aqueous composition having a pH of between 2 and 10 and containing one or more cosmetically acceptable adjuvants chosen from anionic, cationic or nonionic surface-active agents or their mixtures, organic solvents, anionic, nonionic, cationic or amphoteric polymers or their mixtures, thickening agents, penetrating agents, sequestering agents, antioxidants, buffers, dyes and perfumes.

9. Process according to claim 7, characterised in that the composition (A) and/or the composition (B) is provided in the form of an anhydrous composition containing one or more anhydrous solvents and one or more anhydrous surface-active agents, in proportions of at least 15% of solvent and at least 20% of surface-active agent.

10. Process according to claim 9, characterised in that the anhydrous solvent is chosen from C$_2$-C$_{20}$ saturated monoalcohols, polyols, glycol ethers, glycol esters, esters of fatty acids of (sic) lower alcohols.

11. Process according to claim 7, characterised in that the composition (A) and/or the composition (B) is provided in the form of a powder, to be diluted with a liquid at the time of use, consisting of starchy or mucilaginous substances or of powders or flours chosen from silicas, clays, plants pulverised after extracting their active ingredients with solvents.

12. Process according to claim 11, characterised in that a cataplasm is prepared from the composition (A) and/or the composition (B) in the form of a powder, by adding a cosmetically acceptable liquid in sufficient proportions in order to obtain a viscosity of 0.3 to 5 Pa.s.

13. Process according to claim 1, characterised in that the components (A) and (B) are mixed immediately before use, in that the resulting composition is immediately applied to keratinous fibers, in that it is allowed to act for 5 to 40 minutes; the keratinous fibers then being rinsed, washed with shampoo, rinsed again and then dried.

14. Process according to claim 1, characterised in that it comprises the application to the keratinous fibers of the component (A) followed or preceded by the application to the said fibers of the component (B) in that each component is allowed to act for 5 to 40 minutes, in that rinsing with water is optionally carried out between each application; the keratinous fibers then being rinsed, washed with shampoo, rinsed again and then dried.

15. Agent for dyeing keratinous fibers, and in particular hair, characterised in that it comprises the components (A) and (B) as defined in claim 1 in separate form; the components (A) and (B) being intended to be either mixed immediately before use, or to be applied successively to the fibers to be treated.

16. Multi-compartment device or "dyeing kit", characterised in that it comprises at least two compartments, one of which contains the component (A) such as defined in claim 1, and the second contains the component (B) such as defined claim 1.

17. Device according to claim 16, characterised in that the component (A) and/or the component (B) is provided in the form of an anhydrous composition and in that it comprises a third compartment containing a cosmetically acceptable aqueous medium suitable for dyeing, intended to be mixed before use in one or in the first two compartments containing each component (A) or (B).

* * * * *